(12) United States Patent
Bogdanović et al.

(10) Patent No.: US 6,221,285 B1
(45) Date of Patent: Apr. 24, 2001

(54) PRODUCTION OF ORGANOMAGNESIUM COMPOUNDS USING CATALYSTS

(75) Inventors: Borislav Bogdanović; Manfred Schwickardi, both of Mülheim an der Ruhr (DE)

(73) Assignee: Studiengesellschaft Kohle mbH, Mulheim an der Ruhr (DE)

(*) Notice: Subject to any disclaimer, the term of this patent is extended or adjusted under 35 U.S.C. 154(b) by 0 days.

(21) Appl. No.: 09/581,874

(22) PCT Filed: Dec. 10, 1998

(86) PCT No.: PCT/EP98/08056

§ 371 Date: Jun. 19, 2000

§ 102(e) Date: Jun. 19, 2000

(87) PCT Pub. No.: WO99/33844

PCT Pub. Date: Jul. 8, 1999

(30) Foreign Application Priority Data

Dec. 23, 1997 (DE) .............................. 197 57 499

(51) Int. Cl.[7] .............................. C07F 3/02; B01J 27/00
(52) U.S. Cl. ............... 260/665 G; 502/150; 502/167; 556/1; 556/45; 556/113; 556/146
(58) Field of Search ................. 260/665 G; 502/150, 502/167; 556/1, 45, 113, 146

(56) References Cited

U.S. PATENT DOCUMENTS

| 3,161,689 | * | 12/1964 | Cooper et al. | 260/665 |
|---|---|---|---|---|
| 3,449,451 | * | 6/1969 | Senatore | 260/665 |
| 3,597,488 | * | 8/1971 | Shepherd | 260/665 G |
| 3,758,620 | * | 9/1973 | Vit | 260/665 G |
| 5,093,046 | * | 3/1992 | Kober et al. | 260/665 G |
| 5,358,670 | * | 10/1994 | Turnbull et al. | 260/665 G |
| 6,117,372 | * | 9/2000 | Bogdanovic et al. | 260/665 G |

FOREIGN PATENT DOCUMENTS

| 24 55 300 | 6/1979 | (DE) . |
|---|---|---|
| 196 28 159 | 1/1998 | (DE) . |

* cited by examiner

*Primary Examiner*—Porfirio Nazario-Gonzalez
(74) *Attorney, Agent, or Firm*—Norris McLaughlin & Marcus

(57) ABSTRACT

The preparation of organomagnesium compounds from organic halides, especially aromatic chloro compounds, and magnesium metal in the presence of a transition metal compound as a catalyst.

12 Claims, No Drawings

PRODUCTION OF ORGANOMAGNESIUM COMPOUNDS USING CATALYSTS

The present invention relates to a process for the preparation of organomagnesium compounds from organohalides and magnesium metal in the presence of catalysts.

Grignard compounds are usually prepared by reacting organic halides with magnesium in an ethereal solvent; in certain cases, they can also be prepared in hydrocarbons (Comprehensive Organometallic Chemistry II, Vol. 1, 1995, p. 58–63; Comprehensive Organometallic Chemistry I, Vol. 1, 1982, p. 155; Chem. Ber. 1990, 123, 1507 and 1517; Houben-Weyl, Methoden der organischen Chemie, 1973, 13/2a, 53–192).

However, there is a wide variety of organic halogen compounds, including, in particular, aromatic and vinylic chloro compounds, with which the Grignard reaction proceeds hesitantly, with low yields, poorly or not at all. For increasing the reactivity of magnesium towards such halides, numerous methods are known which are based on physical (grinding, ultrasonication, metal vaporization) or chemical (entrainment method, Rieke method, dehydrogenation of magnesium hydride, reversible binding of magnesium anthracene) activation of magnesium (Active Metals—Preparation, Characterization, Applications, Ed. A. Furstner, Verlag Chemie, 1996). As catalysts for the Grignard reaction, anthracene or magnesium anthracene and their derivatives are known; however, they can be employed only in the case of allyl, propargyl and benzyl halides (Chem. Ber. 1990, 123, 1507). There are drawbacks in the mentioned methods in that they are either relatively tedious and expensive or subjected to limitations in application or effectiveness, or result in an increased consumption of magnesium (entrainment method: J. Org. Chem. 1959, 24, 504). Therefore, there is still a need for effective and economical methods for the preparation of Grignard compounds from the above mentioned inert organic halogen compounds which are not subject to the mentioned drawbacks, and with the proviso that conventional, commercially available magnesium grades can be used.

Surprisingly, it has now been found that the addition of suitable metal compounds, optionally in combination with cocatalysts, results in a successful conversion of organic halogen compounds, especially of aromatic chloro compounds and chlorine-containing heterocycles, and other poorly reactive organic chloro compounds to the corresponding Grignard compounds using magnesium metal, e.g., in the form of commercially available Mg powders or turnings, in part with very high yields. Such systems are considered catalytically active when based on compounds of Periodic Table group 3–12 transition metals in which elements of groups 15 or 16 of the Periodic Table, preferably N or O, are bound to the metal. Particularly effective are catalysts containing Mn, Fe, Co or Cu with alkoxy, aryloxy, amido or phthalocyano groups. Useful cocatalysts include, in particular, magnesium halides and anthracenes or substituted anthracenes and their Mg adducts. The process is preferably performed in ethereal solvents, e.g., THF, diglyme and monoglyme. The reactions with organochlorine compounds are preferably performed at from room temperature to the boiling temperature of the solvent.

The invention is further illustrated by way of the following Examples without being limited thereto. The experiments described hereinafter were performed in an argon atmosphere. Anhydrous solvents deprived of air were employed. THF is conveniently dried over magnesium anthracene 3 THF. In all experiments, commercially available Mg powder (270 mesh) was used. For this purpose, anhydrous $MgCl_2$ was prepared from 1,2-dichloroethane and magnesium powder in THF.

EXAMPLE 1

Preparation of the Grignard Compound of 1,3-dibenzyl-2-(4-chlorophenyl)-imidazolidine with Fe(OEt)$_2$ and Isolation Thereof as a TMS Product To 1.25 g (51.4 mmol) of magnesium powder (270 mesh) were added 8 ml of THF and 4 drops of ethyl bromide, and the mixture was stirred at room temperature for 1.5 h. Then, 120 mg (0.82 mmol) of iron(II) ethanolate was added, followed by stirring at room temperature for 30 min during which the solution turned to a dark-brown color. The mixture was heated at 45° C. in an oil bath, and at the same temperature, 12.0 g (33.1 mmol) of 1,3-dibenzyl-2-(4-chlorophenyl)imidazolidine in 23 ml of THF was added dropwise within 1 h with vigorous stirring. The mixture was stirred at 45° C. for another 4 h, and after cooling, filtered through a D4 frit. To the filtrate was added 6.0 ml (47 mmol) of chlorotrimethylsilane dropwise within 30 min upon which an exothermic reaction occurred. The mixture was stirred at room temperature for another several hours, concentrated in an oil-pump vacuum, and the remaining residue was dried at 20° C./0.1 mbar for 15 min. The residue was subsequently extracted with pentane under argon, the precipitate was filtered off through a D4 frit, and the slightly yellow filtrate was concentrated in an oil-pump vacuum. After 2 hours of drying at 20° C./0.1 mbar, 11.3 g of a slightly yellowish powder was obtained. The purity of the isolated 1,3-dibenzyl-2-(4-trimethylsilylphenyl)-imidazolidine (see equ.), which was identified by MS, IR and NMR spectra, was 94.3% from a gas-chromatographical analysis which corresponds to a total yield of 80%.

In a comparative experiment without the addition of a catalyst, the yield of Grignard compound after 4 h was <10%.

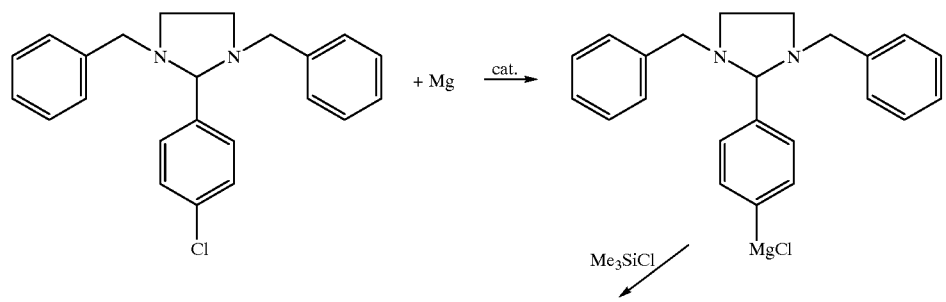

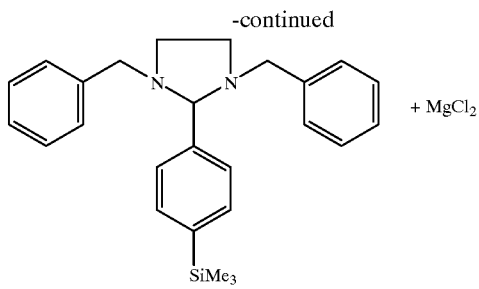

+ MgCl₂

EXAMPLE 2

Catalytic Preparation of 2-methylphenylmagnesium chloride With Manganese Phthalocyanine To 1.85 g (76 mmol) of magnesium powder were added 10 ml of THF and 4 drops of ethyl bromide, and the mixture was stirred at room temperature for 1 h. Then, 560 mg (0.99 mmol) of manganese phthalocyanine (see below) was added, followed by stirring at room temperature for 40 min during which the mixture turned to a deep dark-violet color. The mixture was diluted with about 20 ml of THF, and 5.9 ml (50 mmol) of 2-chlorotoluene (over molecular sieve) was added dropwise within 1 h. The reaction mixture heated to the boiling temperature of the solvent and was further stirred for a total of 4 h. The yield of 2-methylphenylmagnesium chloride was 99% (based on the amount of 2-chlorotoluene employed) as seen from an acidimetric titration of the filtered solution.

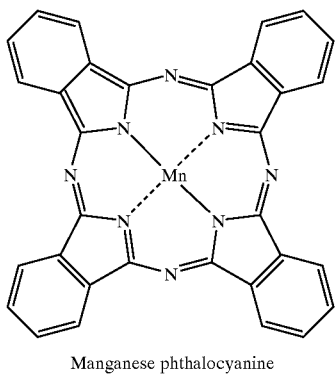

Manganese phthalocyanine

EXAMPLES 3 TO 7

The experiments were conducted by analogy with Example 2 wherein various iron catalysts without a cocatalyst were employed. Instead of chlorotoluene, 1-chloronaphthalene and 2-chloropyridine were converted to the corresponding Grignard compounds.

TABLE 1

| Catalyst | Educt | Reaction time, h | Reaction temp., °C. | Yield of Grignard comp., % |
|---|---|---|---|---|
| 5,10,15,20-Tetraphenyl-21H,23H-porphine/iron(III) chloride complex | 1-Chloro-naphthalene | 2 | 20–66 | 95 |

TABLE 1-continued

| Catalyst | Educt | Reaction time, h | Reaction temp., °C. | Yield of Grignard comp., % |
|---|---|---|---|---|
| Iron phthalocyanine chloride | 1-Chloro-naphthalene | 2 | 20–66 | 87 |
| Iron phthalocyanine | 1-Chloro-naphthalene | 2 | 20–66 | 86 |
| Iron(II) ethanolate | 1-Chloro-naphthalene | 4 | 20–55 | 59 |
| Iron(II) ethanolate | 2-Chloro-pyridine | 0.5 | 20–66 | 98 |

EXAMPLE 8

Catalytic Preparation of 1-naphthylphenylmagnesium chloride With Fe(OEt)₂ and MgCl₂

To 1.85 g (76 mmol) of magnesium powder were added 10 ml of THF and 4 drops of ethyl bromide, and the mixture was stirred at room temperature for 1 h. Then, 135 mg (0.92 mmol) of iron(II) ethanolate was added, followed by stirring for 45 min during which the solution turned to a dark-brown color. Now, 6.5 ml (2.5 mmol) of a 0.384 M magnesium chloride solution in THF as a cocatalyst and about 10 ml of THF were added, followed by stirring at room temperature for another 15 min. Subsequently, 6.8 ml (50 mmol) of 1-chloronaphthalene was added dropwise to the reaction mixture within 1 h, upon which the reaction temperature rose to 60° C. The mixture was stirred at room temperature for another 2 h, and then 2.0 ml of the filtered solution (vol. =34 ml) was titrated acidimetrically. The yield of 1-naphthylmagnesium chloride was 63% (based on the amount of 1-chloronaphthalene employed). 5.0 ml of the filtrate was protolyzed with ethanol, and the volatile components were distilled over in a high vacuum (bath temp. of up to 180° C.). In the distillate, 0.58 g of naphthalene was detected by gas chromatography (=61.5%, based on 1-chloronaphthalene).

If the reaction just described is performed without the addition of a catalyst, a reaction of 1-chloronaphthalene with magnesium powder does not take place within 10 h at room temperature.

EXAMPLES 9–15

The experiments were conducted by analogy with Example 8 wherein various transition metal catalysts were employed in addition to MgCl₂ as a cocatalyst. In addition to 1-chloronaphthalene, p-chlorotrifluorotoluene and neopentyl chloride were also converted to the corresponding Grignard compounds.

TABLE 2

| Catalyst | Educt | Reaction time, h | Reaction temp., ° C. | Yield of Grignard comp., % |
| --- | --- | --- | --- | --- |
| Iron(III) acetylacetonate | 1-Chloro-naphthalene | 3 | RT | 12 |
| Titanium tetra-n-butylate | 1-Chloro-naphthalene | 4 | 20–54 | 36 |
| 5,10,15,20-Tetraphenyl-21H,23H-porphine/cobalt(II) complex (see below) | 1-Chloro-naphthalene | 0.5 | 20–66 | 69 |
| 5,10,15,20-Tetraphenyl-21H,23H-porphine/copper(II) complex | 1-Chloro-naphthalene | 4 | 20–66 | 78 |
| 5,10,15,20-Tetraphenyl-21H,23H-porphine/zinc complex | 1-Chloro-naphthalene | 4 | 20–51 | 58 |
| Iron(II) ethanolate | p-Chloro trifluorotoluene | 6 | 20–39 | 25 |
| Iron(II) ethanolate | Neopentyl chloride | 2 | 20–60 | 96 |

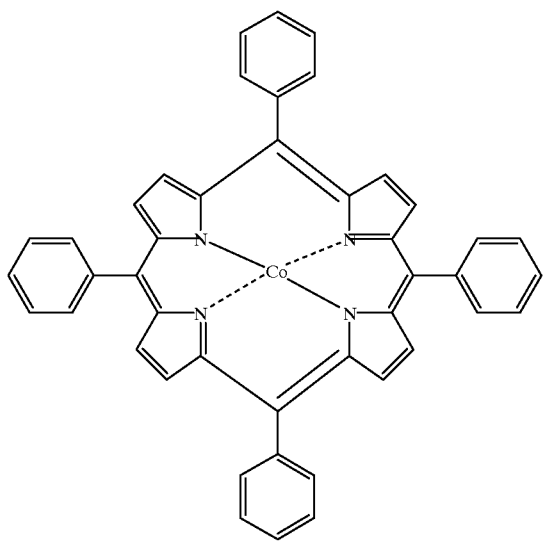

5,10,10,20-Tetraphenyl-21H,23H-porphine/cobalt(II) complex

What is claimed is:

1. A process for the preparation of Grignard compounds, characterized in that organic halides are reacted with magnesium metal in a solvent in the presence of catalysts consisting of compounds of Periodic Table group 3–11 transition metals in which one or more elements of groups 15 or 16 are bound to the metal.

2. The process according to claim 1, characterized in that one or more cocatalysts are additionally employed.

3. The process according to claim 2, wherein anthracene or substituted anthracenes or their Mg adducts and/or magnesium halides are used as said cocatalysts.

4. The process according to claim 2, wherein $MgCl_2$ is used as a cocatalyst.

5. The process according to claim 1, wherein aromatic chloro compounds or chlorine-containing heterocycles are used as organic halides.

6. The process according to claim 1, wherein ethereal solvents are used as the solvent.

7. The process according to claim 6, wherein tetrahydrofuran, monoglyme or diglyme are used as ethereal solvents.

8. The process according to claim 1, wherein Fe, Mn, Co or Cu are used as transition metals.

9. The process according to claim 1, wherein N or O are used as elements of groups 15 or 16.

10. The process according to claim 9, wherein N or O are bound to the metal in the form of amides or phthalocyanines or in the form of alkoxy or aryloxy groups.

11. The process according to claim 1, wherein the reaction is performed at temperatures of up to the boiling temperature of the solvent employed.

12. The process according to claim 1, wherein finely divided magnesium powder is used as the magnesium metal.

* * * * *